(12) United States Patent
Kibler et al.

(10) Patent No.: US 11,135,427 B2
(45) Date of Patent: Oct. 5, 2021

(54) INTERLEAVED MULTI-CONTACT NEUROMODULATION THERAPY WITH REDUCED ENERGY

(71) Applicant: BIOTRONIK SE & CO. KG, Berlin (DE)

(72) Inventors: Andrew B. Kibler, Lake Oswego, OR (US); Sean Slee, Tigard, OR (US); Pamela Shamsie Victoria Riahi, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 111 days.

(21) Appl. No.: 16/569,160

(22) Filed: Sep. 12, 2019

(65) Prior Publication Data

US 2020/0086123 A1    Mar. 19, 2020

Related U.S. Application Data

(60) Provisional application No. 62/730,574, filed on Sep. 13, 2018, provisional application No. 62/741,573, filed on Oct. 5, 2018.

(51) Int. Cl.
*A61N 1/36* (2006.01)

(52) U.S. Cl.
CPC ..... *A61N 1/36071* (2013.01); *A61N 1/36062* (2017.08); *A61N 1/36157* (2013.01); *A61N 1/36175* (2013.01)

(58) Field of Classification Search
None
See application file for complete search history.

(56) References Cited

U.S. PATENT DOCUMENTS

| | | |
|---|---|---|
| 2013/0261706 A1 | 10/2013 | Mirro et al. |
| 2014/0243924 A1 | 8/2014 | Zhu et al. |
| 2014/0350633 A1* | 11/2014 | Gustafson ......... A61N 1/36007 607/41 |
| 2016/0287875 A1 | 10/2016 | Thacker et al. |
| 2017/0001014 A1 | 1/2017 | Griffith |
| 2017/0224989 A1* | 8/2017 | Schepis ............... A61N 1/0556 |
| 2018/0056073 A1 | 3/2018 | Torgeson |
| 2018/0214701 A1* | 8/2018 | Zhang ............... A61N 1/36132 |
| 2018/0289965 A1 | 10/2018 | Nelson et al. |
| 2019/0175904 A1 | 6/2019 | Baru et al. |

* cited by examiner

*Primary Examiner* — Paula J Stice
(74) *Attorney, Agent, or Firm* — Laurence A. Greenberg; Werner H. Stemer; Ralph E. Locher

(57) ABSTRACT

A medical device for generating electrical stimulation of a patient includes: a pulse generator configured to generate current pulses for electrical stimulation of the patient, and at least one electrode lead configured to be connected to the pulse generator. The electrode lead has a plurality of electrode contacts for delivering the current pulses to tissue of the patient. The pulse generator is configured to generate the current pulses with a rate in the range from 1 Hz to 100 kHz, and the individual current pulse has a pulse width in a range from 10 μs to 10 ms.

20 Claims, 18 Drawing Sheets

INTERLEAVED MULTI-CONTACT NEUROMODULATION THERAPY WITH REDUCED ENERGY

CROSS-REFERENCE TO RELATED APPLICATION

This application claims the benefit, under 35 U.S.C. § 119(e), of provisional patent applications Nos. 62/741,573, filed Oct. 5, 2018, and 62/730,574, filed Sep. 13, 2018; the prior applications are herewith incorporated by reference in their entirety.

BACKGROUND OF THE INVENTION

Field of the Invention

The present invention relates to a medical device and a method for controlling electrical stimulation pulses using a lead that comprises a plurality of electrodes.

Within the field of neuromodulation, spinal cord stimulation (SCS) is applied as a means of pain relief for patients suffering from neuropathic pain. SCS has traditionally been thought of as requiring paresthesia sensations to overlap a patient's region of pain in order to provide relief. Recent research has shown that an alternate mechanism of pain relief is available in which high-frequency paresthesia-free stimulation is effective in patients without requiring intra-operative electrode mapped selection.

Particularly, electrical stimulation requires charge balancing to terminate electrochemical reactions that may cause hazardous conditions for both tissue and electrodes. High frequency (HF) stimulation is constrained in timing requiring active balance phases instead of the passive balance phases utilized in traditional 40 to 60 Hz SCS. At 10,000 Hz (10 kHz), the timing between the stimulating and balance phase (i.e. the inter-pulse interval) is very short causing the balance phase amplitude to influence the effect desired to be caused by the stimulating phase. This implies that higher energy is required which translates into frequent device recharges and large implantable device size to fit larger batteries to support continuous stimulation.

Furthermore, the high energy requirements are currently mitigated by stimulation across a single bipolar electrode pair, or a similar small number of electrodes. This can lead to failures in therapy efficacy as the patient's pain region enlarges over time, as well as additional office visits to reprogram to attempt to cover the larger pain area.

These drawbacks are associated with higher patient burden of recharging and travel, an increased chance of uncomfortable implantable device pocket placement or device erosion through the skin due to its large size, a reduced service time requiring the patient to have revision surgeries more often for device replacement, and overall decreased efficacy and patient satisfaction with the implant.

Published patent application US 2017/001,014 A1 describes a stimulation method using electrodes, wherein a charge balancing pulse is distributed over more than one electrode.

Furthermore, 10 kHz paresthesia-free therapy with stimulation duty cycling and the so-called burst therapy (paresthesia-free in most patients) is known in the state of the art.

10 kHz therapy with duty cycling permits lower charge usage with a given stimulation amplitude due to the recurrent incorporation of time intervals when the stimulation is off between time intervals when the stimulation is on. However, the problem with this approach is that it is possible this also reduces overall pain relief to the patient as a result of the overall reduced therapeutic dose.

Furthermore, burst therapy, while requiring lower energy than 10 kHz therapy, suffers from poorer pain relief performance as evidenced by reported responder rates and levels of reduced pain relief in lower back and leg pain patients.

Furthermore, multiple electrodes 'current steering' drives pulses of stimulation on multiple electrodes simultaneously, and has been found to be potentially inefficient for reaching the dorsal horn region of the spinal cord as a therapy target. Furthermore, complex electronics are usually required to drive multiple fractionated current sources, and while they may be ideal for paresthesia therapy steering, this complexity is not desirable for targeting high frequency stimulation.

SUMMARY OF THE INVENTION

Based on the above, it is therefore an object of the present invention to provide a device and a method for controlling electrical stimulation pulses that enable the patient's burden to be reduced, therapy coverage to be extended, therapy effectiveness to be improved and, in particular, device sizes to be reduced.

With the above and other objects in view there is provided, in accordance with the invention, a medical device for generating electrical stimulation of a patient (particularly spinal cord stimulation), the medical device comprising:

a pulse generator configured to generate current pulses for electrical stimulation of the patient, and at least one electrode lead configured to be connected to the pulse generator and comprising a plurality of electrode contacts for delivering said current pulses to tissue of the patient, wherein the pulse generator is configured to generate said current pulses with a rate in the range from 1 Hz to 100 kHz, and wherein the individual current pulse comprises a pulse width in the range from 10 µs to 10 ms.

According to an embodiment, each individual electrode contact may generate current pulses of said rate.

Furthermore, according to an embodiment, the rate is in the range from 50 Hz to 1470 Hz, and wherein the pulse width is in the range from 30 µs to 1000 µs.

Further, according to an embodiment, the respective current pulse comprises an amplitude in the range from 0.01 mA to 20 mA, preferably in the range from 0.1 mA to 10 mA.

Furthermore, according to an embodiment, the pulse generator is configured to deliver a current pulse between two electrode contacts of said plurality of electrode contacts and a subsequent current pulse between two further electrode contacts of said plurality of electrode contacts before delivering or allowing a charge balancing current between said two electrode contacts.

Particularly in an embodiment, the pulse generator is configured to deliver the current pulses using at least four electrode contacts.

According to a further embodiment, said rate is 1470 Hz and the pulse width is 90 µs, wherein particularly the pulse generator is configured to deliver the current pulses using at least four electrode contacts.

Furthermore, according to an embodiment, said rate is 625 Hz and the pulse width is 200 µs, wherein particularly the pulse generator is configured to deliver the current pulses using at least four electrode contacts.

Furthermore, in an embodiment, said rate is 1470 Hz and the pulse width is 60 µs, wherein particularly the pulse generator is configured to deliver the current pulses using at least four electrode contacts.

Particularly, in an embodiment, said rate is 1470 Hz and the pulse width is 120 µs, wherein particularly the pulse generator is configured to deliver the current pulses using at least four electrode contacts.

Furthermore, according to an embodiment, the pulse generator is configured to successively deliver current pulses via different electrode contacts, wherein for each current pulse at least two charge balancing current pulses are subsequently delivered via the respective electrode contact to reach a charge-balanced state, wherein particularly the respective charge balancing current pulses are delivered simultaneously with a stimulating current pulse delivered via one of the different electrode contacts.

Furthermore, according to an embodiment, said rate is 300 Hz, and the pulse width is 300 µs, wherein particularly the pulse generator is configured to deliver the current pulses using at least 3 electrode contacts.

Furthermore, according to an embodiment, said rate is 556 Hz and the pulse width is 300 µs, wherein particularly the pulse generator is configured to deliver the current pulses using at least 3 electrode contacts.

Particularly, according to an embodiment, said rate is 556 Hz and the pulse width is 90 µs, wherein particularly the pulse generator is configured to deliver the current pulses using at least three electrode contacts.

Particularly, in an embodiment, said rate is 300 Hz and the pulse width is 90 µs, wherein particularly the pulse generator is configured to deliver the current pulses using at least three electrode contacts.

Particularly, in an embodiment, said rate is 50 Hz and the pulse width is 300 µs, wherein particularly the pulse generator is configured to deliver the current pulses using at least three electrode contacts.

Furthermore, according to an embodiment, the respective current pulse is a cathodic current pulse, and/or wherein the respective charge balancing current pulse is an anodic current pulse.

Furthermore, according to an embodiment, the pulse generator is configured to deliver said current pulses to the central nervous system of a patient such that no paresthesia is induced in the patient.

Alternatively, according to an embodiment, the pulse generator is configured to deliver said current pulses to the central nervous system of a patient such that paresthesia is induced in the patient.

Furthermore, according to an embodiment, the at least one electrode lead is configured to be implanted along a spinal cord of a patient and to deliver said current pulses to a longitudinal region of the spinal cord which is greater than one vertebral body of the patient. In other words, the active electrode contacts are adjacent a tissue span greater than one vertebral body.

Further, according to an embodiment, neighboring electrode contacts and/or simultaneously active electrode contacts of the electrode lead are separated by a distance in the range from 7 mm to 14 mm. According to an embodiment, neighboring electrode contacts and/or simultaneously active electrode contacts of the electrode lead are separated by a distance in the range from 6 mm to 6.5 mm measured from the center of the electrode contact to the center of the neighboring electrode contact.

Furthermore, according to an embodiment, the medical device is configured to deliver current pulses during an on-period and to suspend delivery of current pulses during an off-period in an alternating fashion, wherein a time span during which current pulses are actually delivered by the pulse generator in the on-period comprises a length that corresponds to 10% to 100%, particularly to 25% to 100%, particularly to 30% to 100%, particularly to 10% to 60% of the length of the on-period. This value in percentage is also denoted as duty cycling value.

With the above and other objects in view there is also provided, in accordance with the invention, a method for controlling electrical stimulation pulses using a medical device as summarized above. The novel method comprises the steps of:

successively delivering a current pulse via each electrode contact, wherein for each current pulse at least one charge balancing current pulse is subsequently delivered via the respective electrode contact to reach a charge-balanced state, and wherein said current pulses are delivered with a rate in the range from 1 Hz to 100 kHz, and wherein the individual current pulse comprises a pulse width in the range from 10 µs to 10 ms.

Furthermore, according to yet another aspect of the present invention, a medical device for generating electrical stimulation of a patient (particularly in the form of spinal cord stimulation) is disclosed, comprising:

a pulse generator configured to generate current pulses for electrical stimulation of the patient, at least one electrode lead configured to be connected to the pulse generator and comprising a plurality of electrode contacts for delivering said current pulses to tissue of the patient (wherein particularly said tissue comprises the spinal cord according to an embodiment), wherein the pulse generator is configured to repeatedly deliver a current pulse between at least two electrodes (of said plurality of electrode contacts) forming a first group of electrode contacts, wherein the pulse generator is further configured to deliver a charge balancing current pulse after each current pulse such that the respective current pulse is separated from the succeeding charge balancing current pulse by an inter-pulse interval, wherein the respective current pulse comprises an amplitude that has the same absolute magnitude as the succeeding charge balancing current pulse but is of opposite polarity, and wherein the pulse generator is configured to deliver between each current pulse and the succeeding charge balancing current pulse a current pulse delivered between at least two further electrode contacts (of said plurality of electrode contacts) forming a second group of electrode contacts.

According to an embodiment, each individual electrode contact may generate current pulses of said rate. Preferably, the rate is applied with regard to cathodic stimulation pulses.

According to an embodiment of the medical device, the pulse generator is further configured to deliver a charge balancing current pulse between said electrodes of the second group after each current pulse delivered between said electrodes of the second group, wherein the respective current pulse delivered between said electrodes of the second group comprises an amplitude that has the same absolute magnitude than the succeeding charge balancing current pulse delivered between said electrodes of the second group but is of opposite sign.

Furthermore, according to an embodiment of the medical device, the respective current pulse is a cathodic current pulse (i.e. corresponds to a cathodic phase) delivered by an electrical contact forming a cathode, and/or wherein the respective charge balancing current pulse is an anodic charge balancing current pulse (i.e. corresponds to an anodic phase) delivered by an electrical contact forming an anode.

Further, according to an embodiment of the medical device, the electrode contacts of the two groups are arranged one after the other in a longitudinal extension direction of the electrode lead, wherein the pulse generator is configured to deliver said current pulses as cathodic current pulses in a sequential fashion (i.e. as a so-called sequential cathode train), such that each electrode contact of the two groups of electrode contacts delivers a cathodic current pulse following a cathodic current pulse of the previous electrode contact and before an anodic charge balancing current pulse of the previous electrode contact.

According to an embodiment, the pulse generator is configured to deliver cathodic current pulses in a sequential fashion comprising temporal and/or spatial variation, i.e. variations of timing of the pulses and/or choice of electrode contact for delivering a pulse (or location of stimulation).

Particularly, said groups of electrode contacts comprise a first, a second, a third, and a fourth electrode contact (of said plurality of electrode contacts) arranged one after the other in said longitudinal extension direction of the electrode lead, wherein the first group of electrode contacts comprises the first and the third electrode contact, and wherein the second group of electrode contacts comprises the second and the fourth electrode contact such that the two groups overlap (i.e. the second electrode contact of the second group is arranged between the first and the third electrode contact of the first group, and the third electrode contact of the first group is arranged between the second and the fourth electrode contact of the second group).

Furthermore, according to an embodiment, the medical device is an implantable medical device. Particularly, the pulse generator is an implantable pulse generator. Furthermore, particularly the electrode lead is an implantable electrode lead.

According to a further embodiment of the medical device according to the present invention, the pulse generator of the medical device is configured to generate current pulses for spinal cord stimulation, i.e. the medical device is a spinal cord stimulator.

According to a further embodiment of the medical device, said plurality of electrode contacts arranged along the electrode lead amounts to eight electrode contacts. The respective electrode contact can be a cylindrical electrode contact extending in the lead longitudinal direction or annular electrode contact extending in a peripheral direction of the electrode lead, wherein each to neighboring electrode contacts are separated by an electrically insulating material forming a portion of an outer surface of the electrode lead, respectively.

Particularly, according to a preferred embodiment of the device according to the present invention, the pulse generator is configured to deliver current pulses without inducing a paresthesia in a patient receiving the current pulses.

Furthermore, according to an embodiment of the medical device, the pulse generator is configured to deliver the current pulses with a frequency in the range from 200 Hz to 100 kHz.

Further, according to an embodiment, only one electrode contact of said plurality of electrode contacts of the electrode lead is arranged on the electrode lead between the two electrode contacts of the first group, and/or wherein only one electrode contact of said plurality of electrode contacts is arranged on the electrode lead between the two electrode contacts of the second group.

Furthermore, the above-described interleaved electrical stimulation by means of the two groups of electrode contacts is also feasible with more than two pairs or groups of electrodes.

A further aspect of the present invention relates to a method for controlling electrical stimulation pulses, wherein the method particularly uses a medical device according to the present invention (particularly a spinal cord stimulator), wherein the method comprises the steps of:

a) delivering a current pulse between at least two electrode contacts forming a first group of electrode contacts, and thereafter b) delivering a charge balancing current pulse between said electrodes of the first group such that the charge balancing current pulse comprises an amplitude that is of the same absolute magnitude as the amplitude of the preceding current pulse, but of opposite sign to perform charge balancing, and c) delivering a further current pulse after the current pulse and prior to the charge balancing current pulse between at least two electrode contacts forming a second group of electrode contacts.

According to an embodiment, the method further comprises the further step d) according to which a further charge balancing current pulse is delivered between said electrodes of the second group after said further current pulse and after charge-balancing pulse of the first group of electrode contacts, wherein the further charge balancing current pulse comprises an amplitude that is of the same absolute magnitude as the amplitude of the further current pulse but of opposite polarity to perform charge balancing.

According to a further embodiment of the method the steps a) to d) of the method are repeated starting with step a).

Furthermore, according to an embodiment of the method, the current pulses (i.e. the respective current pulse and the respective further current pulse) are delivered as cathodic current pulses in a spatial and temporal sequential fashion (i.e. as a so-called sequential cathode train), such that each electrode contact of the two groups of electrode contacts delivers (as a cathode) a cathodic current pulse following a cathodic current pulse of the previous electrode contact and before an anodic charge balancing current pulse of the previous electrode contact.

In other words, stimulation preferably results in a sequential cathode train, wherein adjacent electrode contacts deliver cathodic stimulation following cathodic stimulation of a previous adjacent cathode and before the previous cathode delivers its anodic charge-balancing phase.

Furthermore, according to an embodiment of the method, the groups of electrode contacts overlap along a longitudinal extension direction of an electrode lead comprising the electrode contacts (see e.g. also above).

According to a further embodiment of the method according to the present invention, the current pulses are delivered with a frequency in the range from 200 Hz to 100 kHz.

Further, according to an embodiment of the method, the current pulses are preferably adapted to perform spinal cord stimulation (SCS).

According to a further embodiment of the method according to the present invention, the electrical stimulation/current pulses are provided without inducing paresthesia (particularly in case of SCS).

According to a further embodiment of the method according to the present invention, electrical stimulation by means of the current pulses is provided to induce electrical field changes in the spinal cord of frequencies from 200 Hz to 100 kHz According to a further embodiment of the method, only one further electrode contact is arranged on the electrode lead between the two electrode contacts of the first group. Furthermore, particularly, only one further electrode contact is arranged on the electrode lead between the two electrode contacts of the second group.

Of course, also regarding the method according to the present invention, the interleaved stimulation described above is feasible with more than two pairs or groups of electrode contacts (see also above).

A further aspect of the present invention relates to a use of the method according to the present invention for configuring or operating a spinal cord stimulator.

Other features which are considered as characteristic for the invention are set forth in the appended claims.

Although the invention is illustrated and described herein as embodied in an interleaved multi-contact neuromodulation therapy with reduced energy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 5A: First phase, first group G1, cathode is superior.
FIG. 5B: Second phase, second group G2, cathode is superior.
FIG. 5C: Third phase, first group G1, cathode is inferior.
FIG. 5D: Last phase, second group G2, cathode is inferior.
The inter-pulse phases where no stimulation is delivered are not shown.

FIG. 8A: Electrode configurations tested;
FIG. 8B: Normalized paresthesia threshold amplitude per configuration;
FIG. 8C: Impedance per configuration;
FIG. 8D: Mean power required to reach paresthesia threshold via dorsal column recruitment per configuration;

DETAILED DESCRIPTION OF THE INVENTION

Traditional paresthesia-based spinal cord stimulation (SCS) therapy makes use of dorsal column axon recruitment to induce a tingling sensation overlapping with the region of nociception and thus reducing the perception and experience of pain. Its effect begins in minutes and the paresthesia sensation is typically tolerated by the patient for the continued reduction of their perception of pain. Patients may adjust the stimulation amplitude using a patient remote control to a greater level to enhance their pain relief during periods of heighted pain, and may reduce the amplitude and sensation of paresthesia during periods of restfulness, decreased pain, or different body positions which influence lead position relative to the spinal cord. Due to the fact that paresthesia is an unnatural sensation, patients generally prefer to use this control to minimize it.

The mechanism of action of paresthesia-based stimulation is as follows: Electrical fields generated by SCS electrode leads over the dorsal columns of the spinal cord induce action potentials in the axially oriented large dorsal column axons which are associated with conduction of sensory information to the brain. These action potentials propagate to the brain, inducing paresthesia sensations, as well as retrograde into the dorsal horn network of the spinal cord grey matter. This retrograde propagation of action potentials reach and stimulate inhibitory interneurons, the excitation of said inhibitory interneurons facilitates inhibition of pain relay neurons.

High-frequency SCS therapy utilizes stimulation frequencies between 1 kHz and 100 kHz to achieve a neuromodulatory effect without recruiting the dorsal column fibers associated with paresthesia. Research indicates that this therapy modality reduces the wind-up hypersensitivity of dorsal horn interneurons responsible for relaying a painful sensation from the peripheral to the central nervous system. Pain relief associated with this stimulation may require several hours to a day to take effect.

Figure 6:
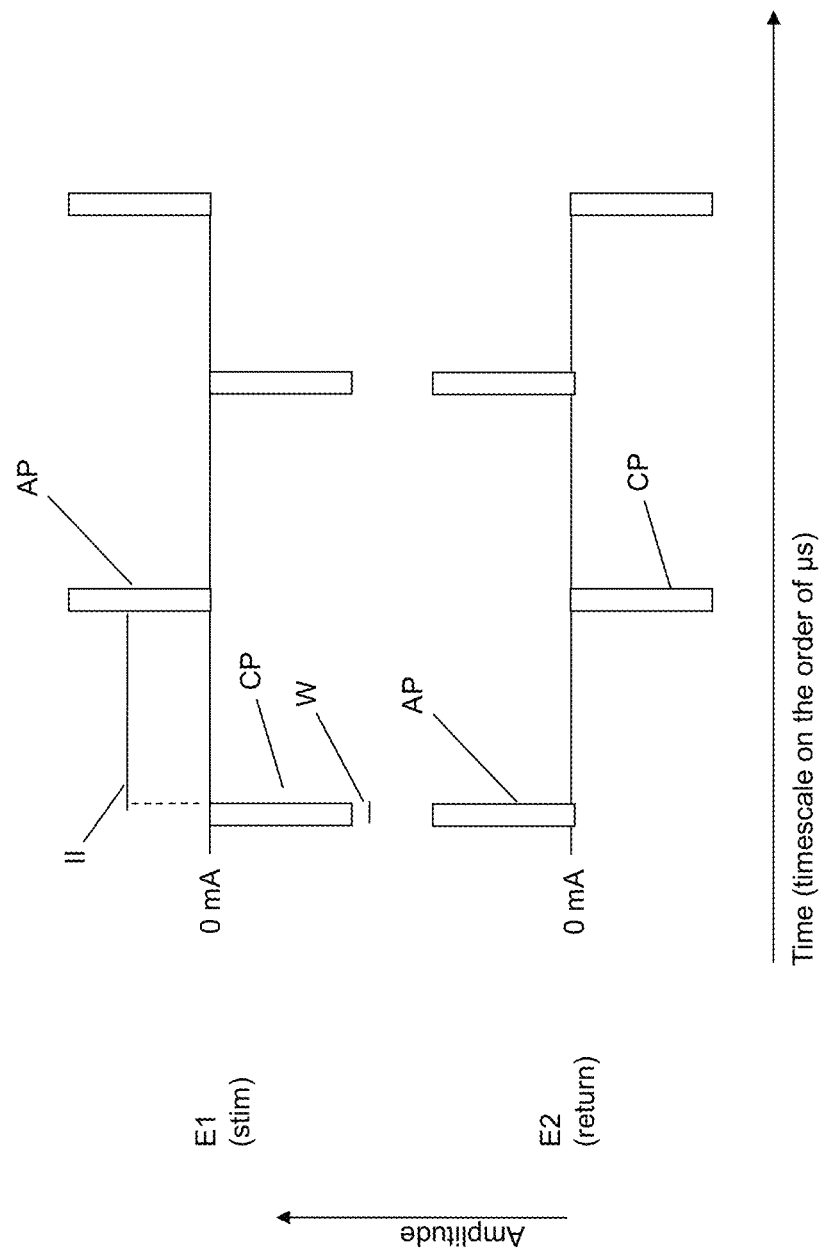
FIG. 6 shows a diagram of a traditional high-frequency stimulation waveform between two electrode contacts; AP denotes the anodic phase, CP the cathodic phase, W the pulse width, II the interpulse interval.

FIG. 6 shows a diagram to illustrate a traditional high-frequency stimulation waveform between two electrodes E1, E2. Stimulation begins with a cathodic phase CP of width W, contains an inter-pulse interval II, and ends with an anodic (charge balancing) phase AP of width W, and repeats. The return electrode E2 passes the same but opposite currents. Additional electrodes may share different amounts of current, but with the same timing and wave shape.

The mechanism of action of this mode of therapy is still under debate; however the prevailing theory is as follows. High-frequency SCS stimulation has little influence on the dorsal column axons which facilitate paresthesia in low-frequency SCS therapy, instead this stimulation is thought to directly induce slight potentiation changes on lamina I neurons in the dorsal horn of the spinal cord. The potentiation changes trigger a cascade of intracellular signaling responses which induce a direct inhibition of sensitization and suppression of activity of neuropathic pain relay neurons in the dorsal horn.

This approach is similar in frequencies to high-frequency transcutaneous spinal electroanalgesia (TSE) which has been available for decades. Whether the underlying mechanisms and site of pain relief action are the same between high-frequency TSE and high-frequency SCS remains to be determined.

During a recent clinical study (cf. FIGS. 8A to 8D), several common combinations of stimulation contacts were tested to determine their paresthesia threshold current with a fixed stimulation waveform parameter set. Impedances were also measured between those contacts in order to allow calculation of a paresthesia threshold power for each electrode contact combination. This portion of the study found that bipolar pairs of adjacent electrode contacts and electrode contact combinations with multiple cathodes (EC603, EC605, EC608) are relatively inefficient stimulation techniques, when compared to a spaced bipole or tripole (EC606, EC607). These findings are applied to the invention disclosed herein, particularly by utilizing spacing between electrode contacts in addition to interleave-delayed charge balancing.

Particularly, the present invention thus provides an SCS stimulation approach that is designed to reduce energy demand while providing equivalent or improved pain relief and broader therapy coverage of pain dermatomal areas compared to existing methods.

Particularly, the present invention can be used with implantable spinal cord stimulators comprising percutaneous electrode or paddle leads implanted in the supra-dural space in the patient's vertebral lumen. Using such leads, the present invention particularly allows to provide SCS to patients by allowing the influence of a single pulse on neuron transmembrane potential to maximally take effect prior to charge balancing (polarity reversal) of the stimulating electrode contact by applying a time delay prior to charge balancing. At the same time, the disclosed stimulation maximizes therapeutic effect of stimulating pulses by delivering pulses of the same polarity on adjacent electrode contacts during this delay time. Particularly, this approach departs from traditional neuromodulation stimulation, wherein each stimulation pulse and its charge balancing phase occur prior to stimulation on another set of electrodes.

Figure 1:
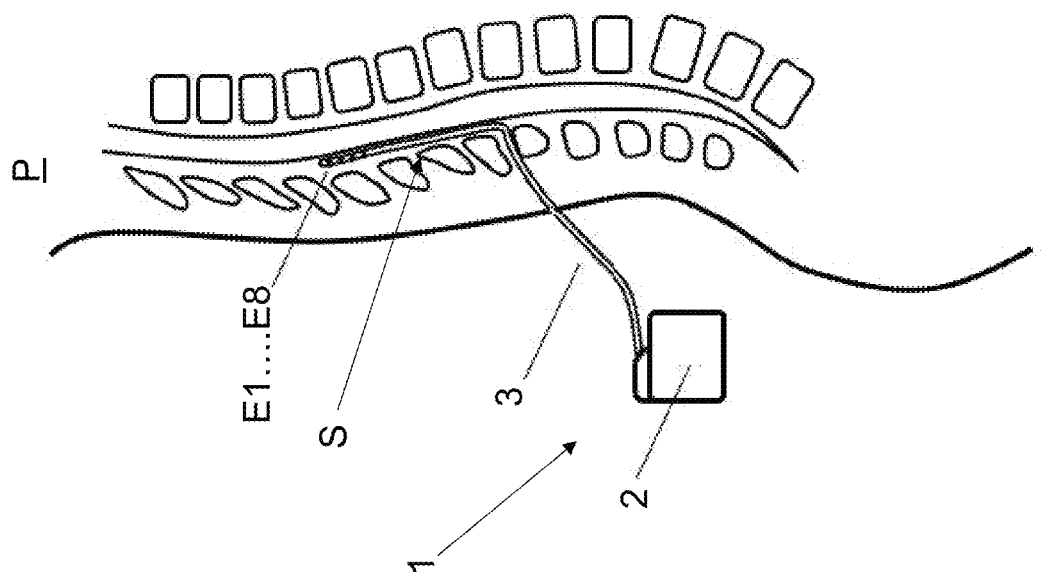
FIG. 1 shows an embodiment of a medical device according to the present invention in form of a spinal cord stimulation device having an electrode lead that can be implanted in a patient's epidural space.
Figure 2:
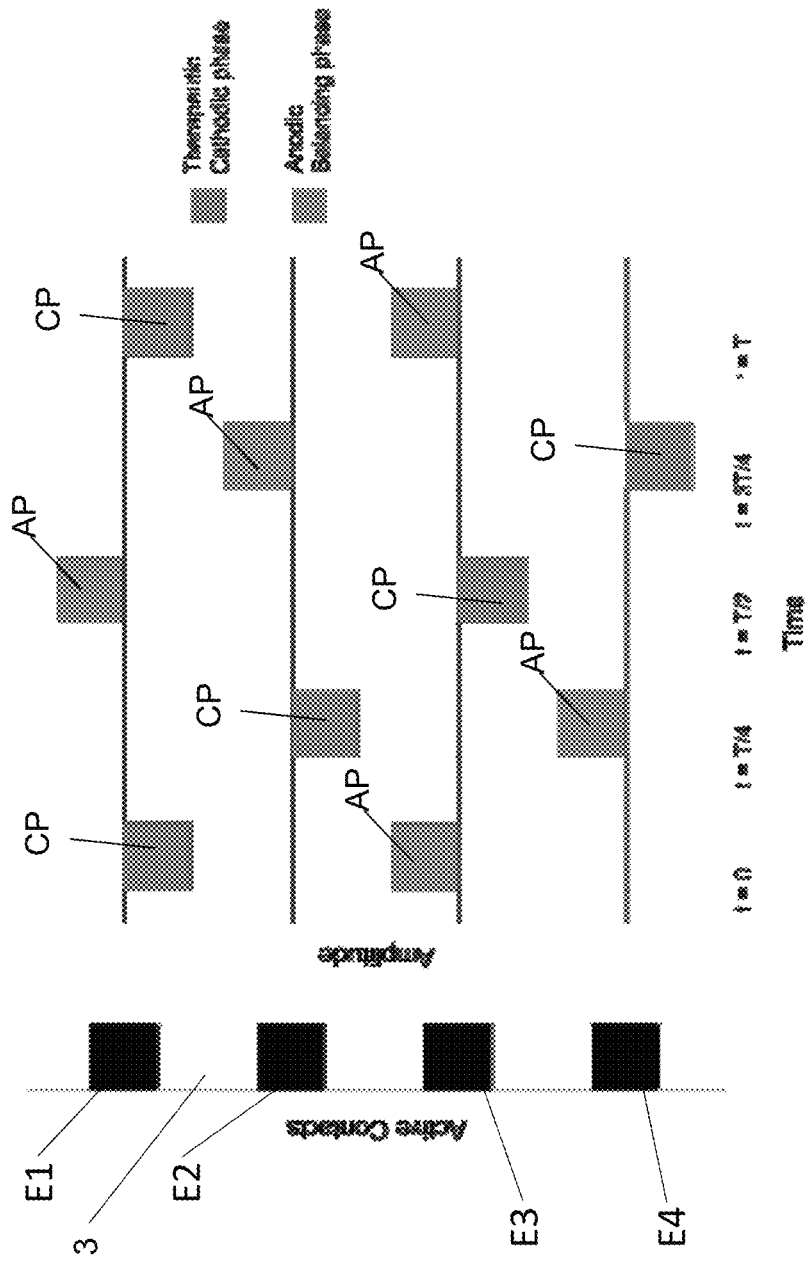
FIG. 2 shows a schematic illustration of an embodiment of the medical device according to the present invention, wherein the pulse generator is configured for dual dipole spinal cord stimulation.

FIG. 1 shows in conjunction with FIG. 2 an embodiment of a medical device 1 for generating electrical stimulation of a patient P, comprising a pulse generator 2 configured to generate current pulses for electrical stimulation of the patient P, and at least one electrode lead 3 configured to be connected to the pulse generator 2 and comprising a plurality of electrode contacts E1, . . . , E8 for delivering said current pulses to tissue S of the patient P, wherein the pulse generator 2 is configured to generate said current pulses with a rate in the range from 1 Hz to 100 kHz, and wherein the individual current pulse comprises a pulse width in the range from 10 µs to 10 ms.

Particularly, as indicated in FIG. 2, the pulse generator 2 of the medical device 1 is configured to deliver a current pulse CP between two electrode contacts E1, E3 of said plurality of electrode contacts and a subsequent current pulse CP between two further electrode contacts E2, E4 of said plurality of electrode contacts before delivering a charge balancing current pulse AP between said two electrode contacts E1, E3 to reach a charge-balanced state.

In this way the medical device 1 according to the present invention realizes a spatial and temporal pattern for power efficient stimulation. The basic concept of this pattern is illustrated in FIG. 2. Particularly, a cathodic current pulse CP is delivered from every active electrode contact E1, . . . , E4 in a sequential pattern during each stimulus period (T=1/frequency). This allows to providing therapeutic (cathodic) current pulse delivery on every stimulation cycle via every active electrode contact E1, . . . , E4 (here four electrode contacts). This increases the spatial extent of therapeutic modulation.

Furthermore, to yield an efficient therapeutic stimulation, the electrode contacts E1, . . . , E4 are preferably spaced apart from one another by ~14 mm measured from the center of one electrode contact to the center of the neighboring electrode contact. It has been found that this electrode contact spacing allows to modulate tissues deeper in the spinal cord at lower current amplitudes compared to the present state of the art.

Furthermore, the so-called dual dipole stimulation shown in FIG. 2 comprises a delayed balancing of the therapeutic current pulses CP on each electrode contact E1, . . . , E4.

Though required for safely avoiding electrochemical reactions in the tissue, the respective anodic charge balancing phase AP may reduce the therapeutic, modulatory effect of the prior cathodic phase CP. By delaying the anodic charge balancing phase AP, its potential to influence the therapeutic effect is reduced.

In a standard 'high density' therapy operating at twice the frequency, thus requiring approximately the same energy (cf. FIG. 6), the therapeutic influence is approximately limited to the region between the active electrode contacts E1, E2. Secondly, the close proximity of the active electrode contacts E1, E2 reduces the penetration depth of therapeutic modulation into the spinal cord. Finally, cathodic modulatory phases CP are rapidly canceled by the subsequent balancing phase AP. This has the potential to reduce therapeutic efficacy.

The dual-dipole spinal cord stimulation according to FIG. 2 has been shown to be particularly effective using e.g. four active electrode contact E1, . . . , E4 with the following rates and pulse widths of the current pulses CP:
    Rate=1470 Hz and pulse width=90 µs,
    Rate=625 Hz and pulse width=200 µs,
    Rate=1470 Hz and pulse width=60 µs, or
    Rate=1470 Hz and pulse width=120 µs.
For these rates and pulse widths the current pulses CP and charge balancing current pulses AP preferably comprise an amplitude in the range from 0.1 mA to 10 mA.

Figure 4:
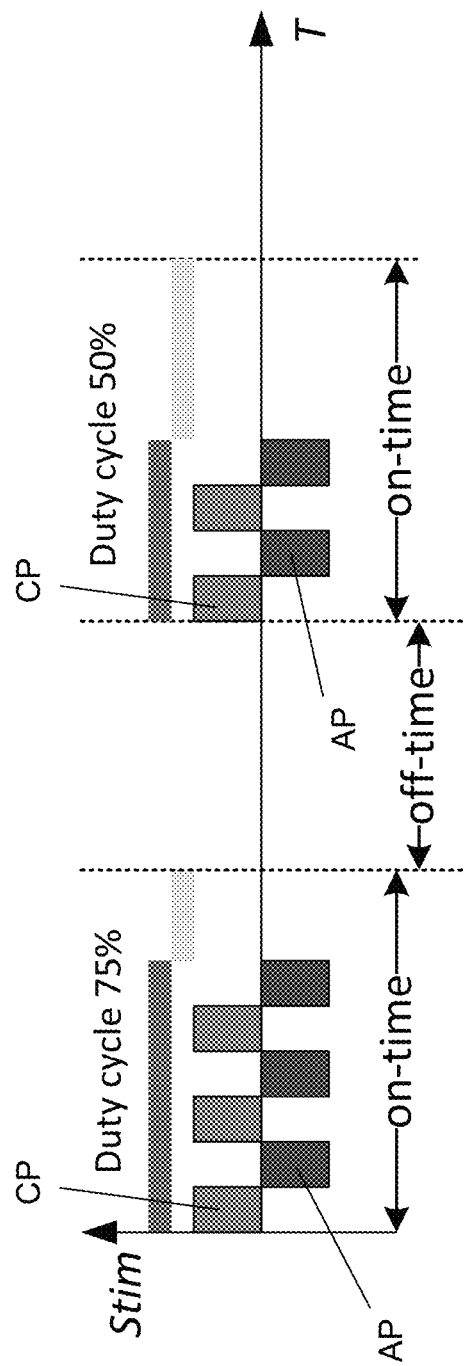
FIG. 4 shows a schematic illustration of the principle of duty cycling that can be used by a medical device according to the present invention.
Figure 5:
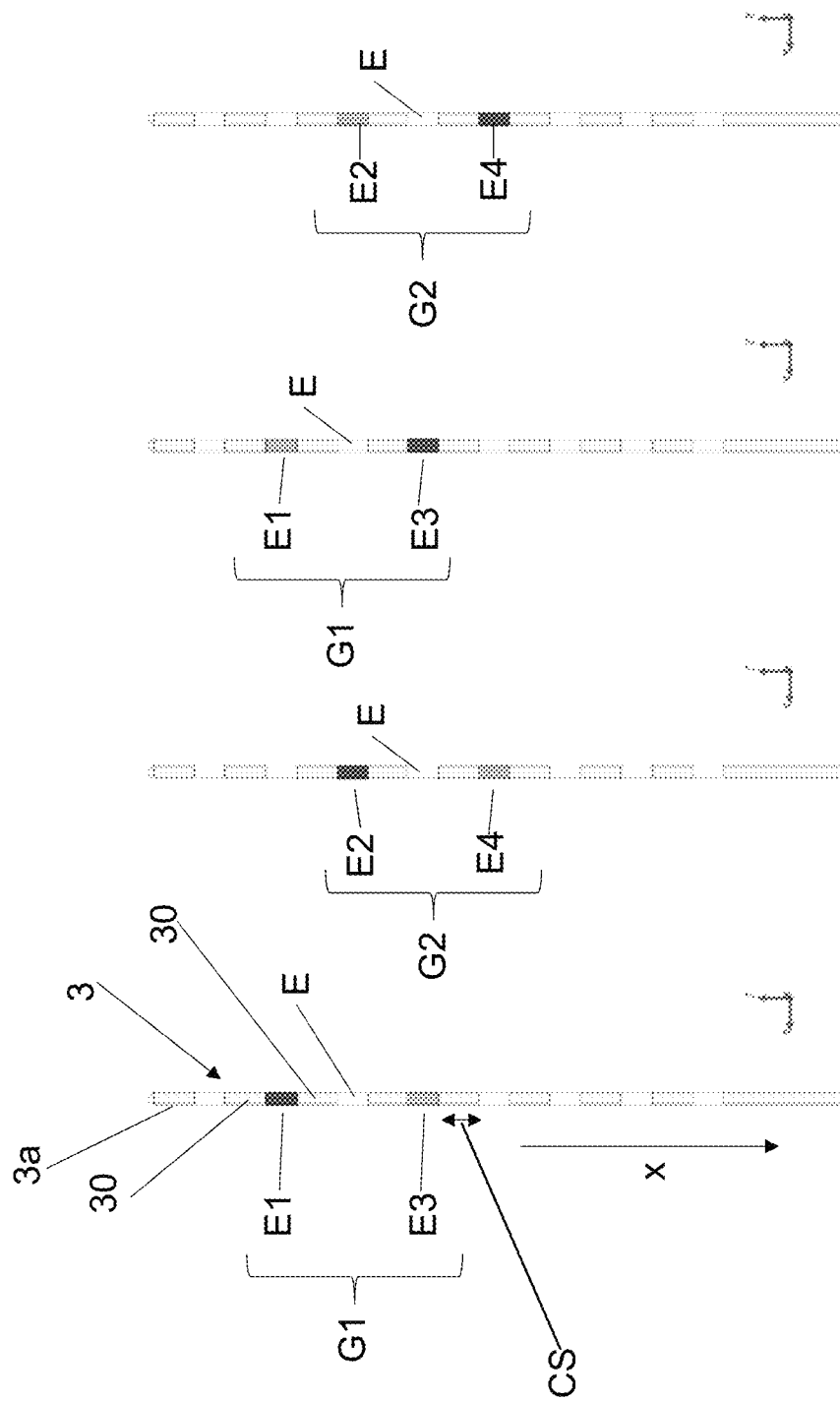
FIGS. 5A to 5D show an electrode lead of an embodiment of a medical device according to the present invention in the form of an 8-contact SCS lead with four active electrode contacts termed E1 to E4, wherein dark and light grey contacts are the active cathode and anode of a given group of electrodes, respectively.

As further shown in FIG. 4, in an embodiment, the medical device 1 according the present invention is configured to deliver current pulses CP during an on-period (on-time) and to suspend delivery of current pulses CP during on off-period (off-time) in an alternating fashion, wherein a time span during which current pulses are actually delivered by the pulse generator 2 in the on-period (on-time) comprises a length that corresponds to 10% to 100% of the length of the on-period, particularly 30% to 100%.

In other words, "duty cycling" means that the pulse generator 2 of the medical device 1 can be programmed that for some phases therapy is ON "on-time", and for some phases therapy is OFF "off-time". The duty cycling value defines how long the therapy is on (in %) within "on-time".

While in the shown embodiments of FIGS. 1 and 2, the number of electrode contacts E1 E2, E3, E4 is limited to four electrode contacts, the number of active electrode contacts preferably lies in the range from 4 to 32.

According to an alternative embodiment shown in FIGS. 1 and 3, the pulse generator 2 is configured to successively deliver a current pulse CP via an associated electrode contact E1, E3, E5, wherein for each current pulse CP at least two charge balancing current pulses AP are subsequently delivered via the respective electrode contact E1, E3, E5 to reach a charge-balanced state. Here, the respective charge balancing current pulse AP is preferably delivered simultaneously to one of the current pulses CP.

Figure 3:
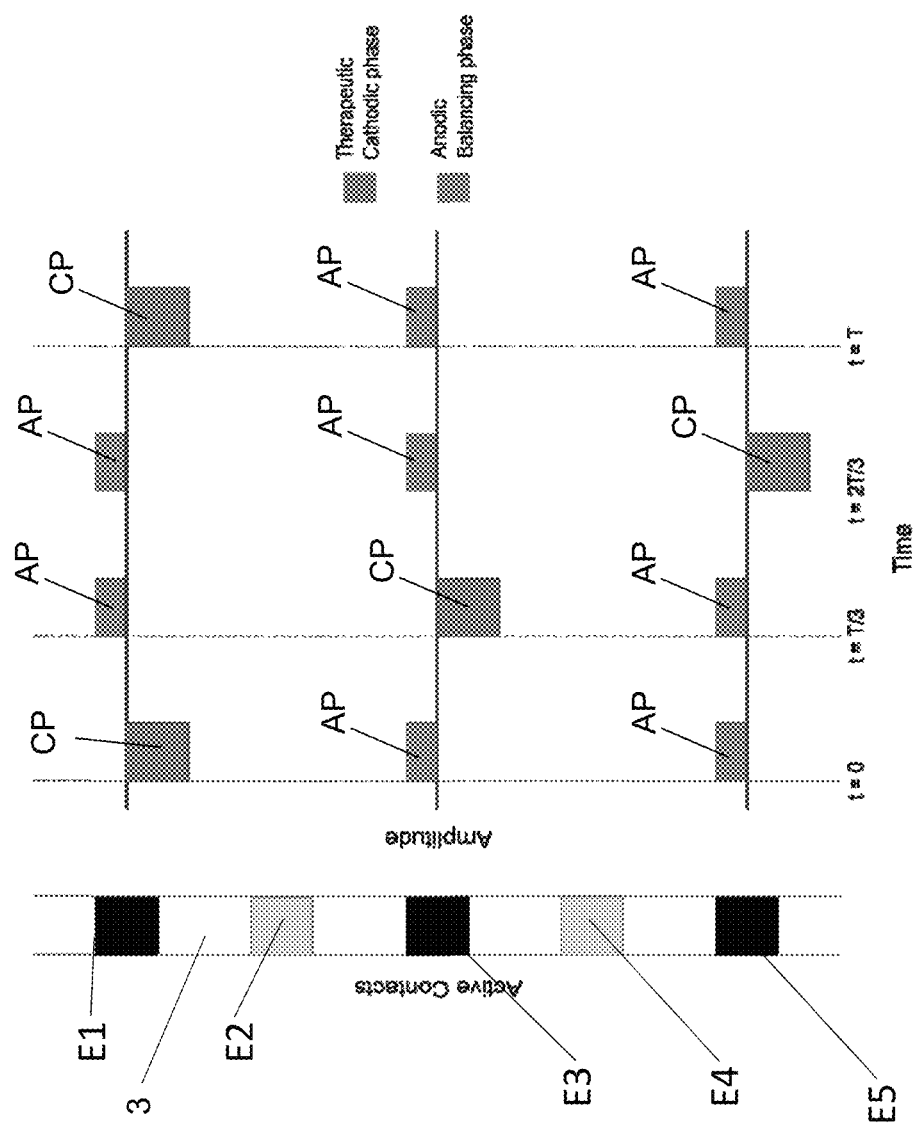
FIG. 3 shows a schematic illustration of an embodiment of the medical device according to the present invention, wherein the pulse generator is configured for dual dipole spinal cord stimulation.

The configuration shown in FIG. 3 is also denoted as rotating cathodes spinal cord stimulation and also realizes a spatial and temporal stimulation pattern for power efficient stimulation. Here a cathodic current pulse CP is delivered from every active electrode contact E1, E3, E5 in a sequential fashion during each stimulus period (T=1/frequency).

This allows to providing a therapeutic (cathodic) current pulse delivery on every stimulation cycle on every active electrode contacts (three electrode contacts E1, E2, E3 spanning the length of five electrode contacts in this example). This increases the spatial extent of therapeutic modulation. Furthermore, the stimulation in the rotating cathode configuration preferably uses an optimal spacing of ~14 mm between active neighboring electrode contacts E1, E3, E5. Furthermore, prior research has shown that this electrode contact spacing allows to modulate tissues deeper in the spinal cord at lower current amplitudes compared to the present state of the art.

Furthermore, the delayed balancing of therapeutic current pulses CP on each electrode contact E1, E3, E4 though required for safely avoiding electrochemical reactions in the tissue, can reduce the therapeutic modulatory effect of the prior cathodic phase. By delaying the anodic charge balancing phase AP, its potential to influence the therapeutic effect is reduced, wherein the anodic current is distributed across multiple electrodes (i.e. two electrodes in FIG. 3). This will increase the area of therapeutic modulation and also reduce the impedance of the electrode configuration (thus reducing power requirements).

The configuration shown in FIG. 3 allows to span a greater number of electrode contacts (greater area of therapeutic influence), and has been shown to yield excellent pain relief (c.f. study BENEFIT-02) using a long pulse width (e.g. 300 µs) and a low rate (e.g. 300 Hz) of the current pulses CP. Longer pulse widths typically produce therapeutic effects at lower current amplitudes. This in combination with low stimulation frequency greatly reduces power requirements.

Particularly, the following parameter values have shown very good results using e.g. three active electrode contacts (E1, E3, E5):
    Rate=300 Hz, and pulse width=300 µs,
    Rate=556 Hz, and pulse width=300 µs,
    Rate=556 Hz, and pulse width=90 µs,
    Rate=300 Hz, and pulse width=90 µs, or
    Rate=50 Hz, and pulse width=300 µs.

Particularly, the above parameters are preferably used with a number of active electrode contacts in the range from three to 32, particularly three to six. Cycling preferably lies in the range from 25%-100% on-time (cf. FIG. 4) and the current pulses preferably comprise an amplitude in the range from 0.01 mA to 20 mA. Particularly one of the active electrode contacts can be a can (housing) of the medical device 1 or a group of other electrode contacts combined together.

EXAMPLES

Particularly, the following measurements have been conducted to evaluate pain relieve using the medical device 1/method according to the present invention;

Example 1: Rotating Cathodes

Here, the subject was implanted with two percutaneous 8-contact SCS leads 3, wherein the lead tip of the first lead was placed at upper T9 and the lead tip of the second lead was placed at lower T9 level. Contact coverage range was between upper T9 and mid T11. Subject experienced lower back and leg pain, selected stimulation electrodes were E4, E6, and E8 (most inferior contact) on the second lead. Subject was given 3-phase multiphasic therapy using 300 Hz and 300 µs, continuous, 1.1 mA amplitude. The Subject baseline pain was 9/10, and the therapy treated pain amounted to 1/10. According to an embodiment, continuous means that the pulsing sequence is all time switches on, with no duty cycling.

Example 2: Dual Dipole

The subject was implanted with two percutaneous 8-contact SCS leads 3, the tip of the first lead was placed at upper T9 and the tip of the second lead was placed at mid T9 level. Contact coverage range was between upper T9 and upper T11. The subject experienced lower back and leg pain, selected stimulation electrodes were E1 (most superior contact), E2, E3, and E4 on the first lead. The subject was given 4-phase multiphasic therapy at 1492 Hz, 90 µs, continuous, 4.8 mA. The subject's baseline pain was 7/10, and the therapy treated pain amounted to 2/10.

Example 3: Rotating Cathodes

Subject was implanted with two percutaneous 8-contact SCS leads 3, wherein the tip of the first lead was placed at lower T7 and the tip of the second lead was placed at mid T8 level. Contact coverage range was between lower T7 and lower T10. The subject experienced lower back and leg pain, selected stimulation electrodes were E4, E6, and E8 (most inferior contact) on the first lead. The subject was given a 3-phase multiphasic therapy at 556 Hz, 300 μs, continuous, 0.7 mA. The subject's baseline pain was 7/10, and the therapy treated pain amounts to 2/10. This subject described improved leg pain with multiphasic therapy which standard 10 kHz 30 μs stimulation could not reach.

Example 4: Dual Dipole

The subject was implanted with two percutaneous 8-contact SCS leads 3, wherein the tip of the first lead was placed at upper T9, and the tip of the second lead was placed at upper T10 level. Contact coverage range was between upper T9 and upper T12. The subject experienced lower back and leg pain, selected stimulation electrode contacts were E1 (most superior contact), E2, E3, and E4 on the second lead. The subject was given a 4-phase multiphasic therapy at 625 Hz, 200 μs, continuous, 0.24 mA. The Subject baseline pain was 9/10, the therapy treated pain amounted to 3/10.

Furthermore, FIG. 1 shows in conjunction with FIGS. 5A to 5D and 7 an embodiment of a medical device 1 according to yet another aspect of the present invention, comprising a pulse generator 2 configured to generate current pulses for electrical stimulation of the patient, an electrode lead 3 configured to be connected to the pulse generator 2 and comprising a plurality of electrode contacts E1 . . . E8 for delivering said current pulses to tissue of the patient P, here the spinal cord S, wherein the pulse generator 2 is configured to repeatedly deliver a current pulse CP between two electrodes E1, E3 forming a first group G1 of electrode contacts of said plurality of electrode contacts, and wherein the pulse generator 2 is further configured to deliver a charge balancing current pulse AP after each current pulse CP between said electrodes of the first group such that the respective current pulse CP is separated from the succeeding charge balancing current pulse AP by an inter pulse interval II, wherein the respective current pulse CP comprises an amplitude A that has the same absolute magnitude A than the succeeding charge balancing current pulse AP but is of opposite sign, and wherein the pulse generator 2 is configured to deliver between each current pulse CP and the succeeding charge balancing current pulse AP delivered between the electrodes of the first group G1 a current pulse CP delivered between two further electrodes E2, E4 forming a second group G2 of electrodes.

Particularly, the pulse generator 2 is further configured to deliver a charge balancing current pulse AP between said electrodes E2, E4 of the second group G2 after each current pulse CP delivered between said electrodes E2, E4 of the second group G2, wherein the respective current pulse CP delivered between said electrodes E2, E4 of the second group G2 comprises an amplitude B that has the same absolute magnitude than the succeeding charge balancing current pulse AP delivered between said electrodes E2, E4 of the second group but is of opposite polarity.

In the present embodiment, 4 active electrode contacts E1 to E4 are used according to FIGS. 5A to 5D that are particularly separated by 7 mm (center-to-center), wherein a corresponding gap between each two neighboring electrodes contacts is filled with an electrical insulating portion 30 forming part of an outer surface 3a of the lead 3.

Particularly, as indicated in FIGS. 5A to 5D said groups G1, G2 of electrode contacts E1 . . . E4 comprise a first, a second, a third, and a fourth electrode contact E1, E2, E3, E4 arranged one after the other in a longitudinal extension direction x of the electrode lead 3, wherein the first group G1 of electrode contacts comprises the first and the third electrode contact E1, E3, and wherein the second group G2 of electrode contacts comprises the second and the fourth electrode contact E2, E4 such that the two groups G1, G2 overlap, i.e. the second electrode contact E2 of the second group G2 is arranged between the first and the third electrode contact E1, E3 of the first group G1, and the third electrode contact E3 of the first group G1 is arranged between the second and the fourth electrode contact E2, E4 of the second group G2.

As further shown in FIGS. 5A to 5D and 7, these electrode contact groups G1, G2 can be used for delivering stimulation from the pulse generator 2 as follows. Here, the two groups G1, G2 form two independent stimulation channels, wherein the first provides stimulation through electrode contacts E1 and E3 and the second through electrode contacts E2 and E4. Each channel G1, G2 provides bipolar constant current stimulation with a symmetric charge balanced waveform. For each electrode contact, the cathodic stimulation phase (current pulse) CP is balanced by an anodic phase (charge balancing current pulse) AP that is delayed by half a cycle, which also serves as cathodic stimulation on the paired electrode contact. Particularly, the two channels or groups G1, G2 provide stimulation at the same frequency but with a period delay of 0.25 of the cycle time period. This results in cathodic stimulation every 0.25 cycles at an anatomically distinct location, thus providing efficient coverage of therapy.

Figure 7:
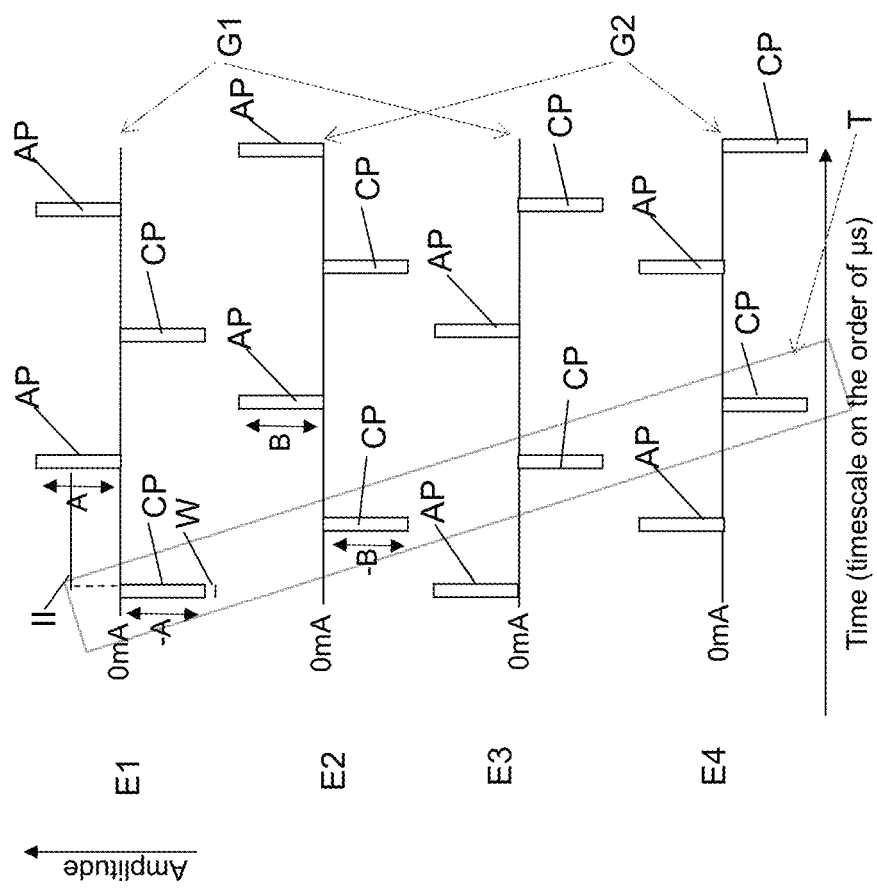
FIG. 7 shows a diagram of a sub-perception stimulation waveform between two groups (G1 and G2) of two electrode contacts (E1, E3 and E2, E4 in G1 and G2, respectively) according to an embodiment of the present invention. AP denotes the anodic phase, CP the cathodic phase, W the pulse width, II the interpulse interval.
Figure 8A:
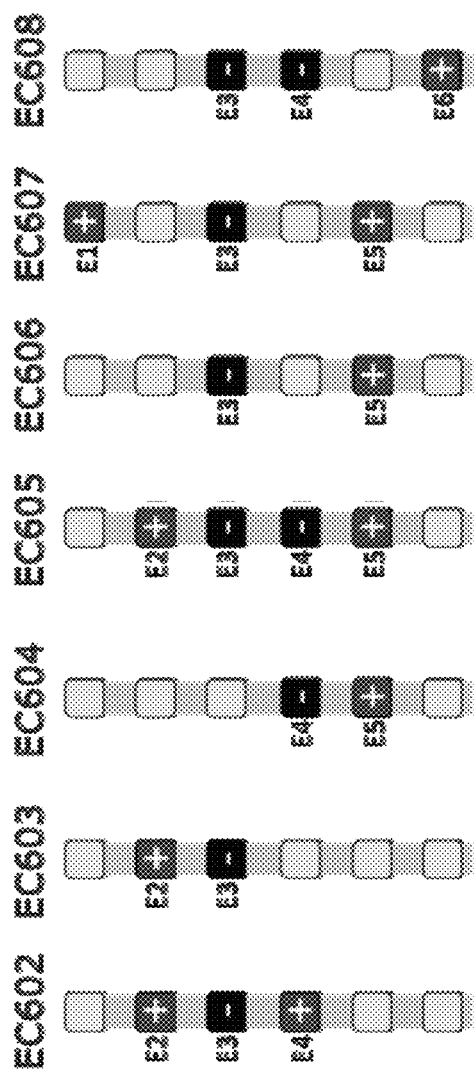
FIG. 8A to 8D show Dorsal Column Recruitment Efficiency as found in the study BENEFIT-01.
Figure 8B:
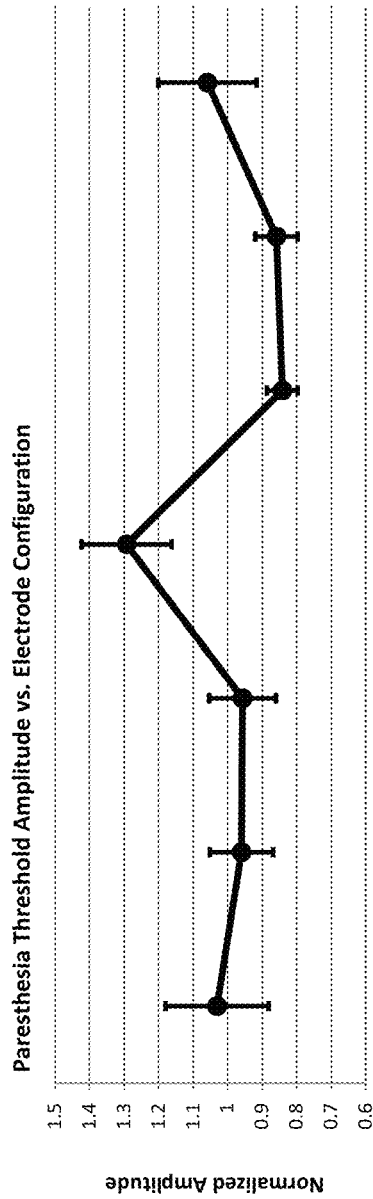
Figure 8C:
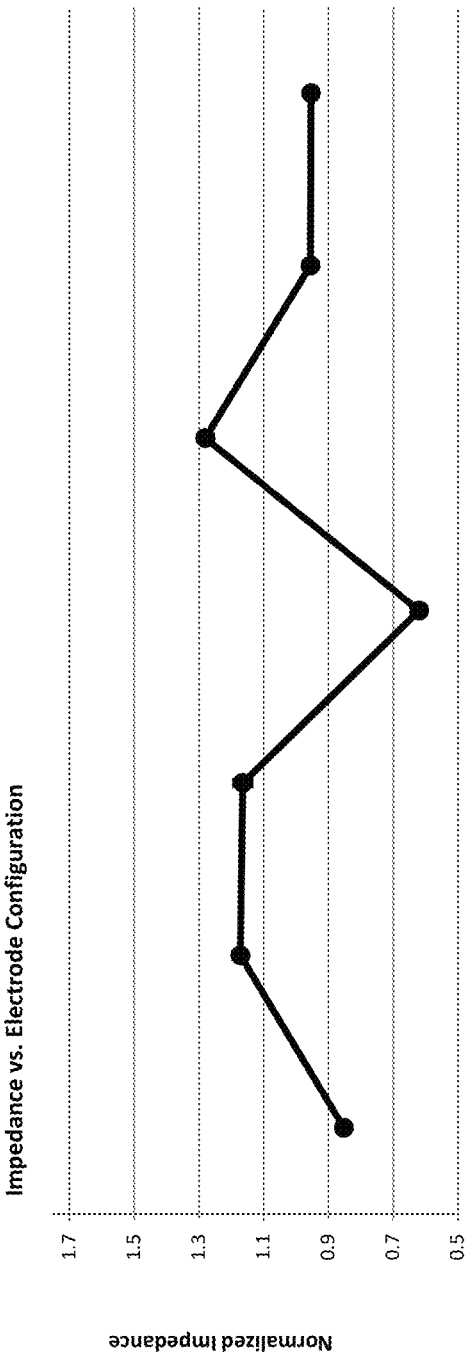
Figure 8D:
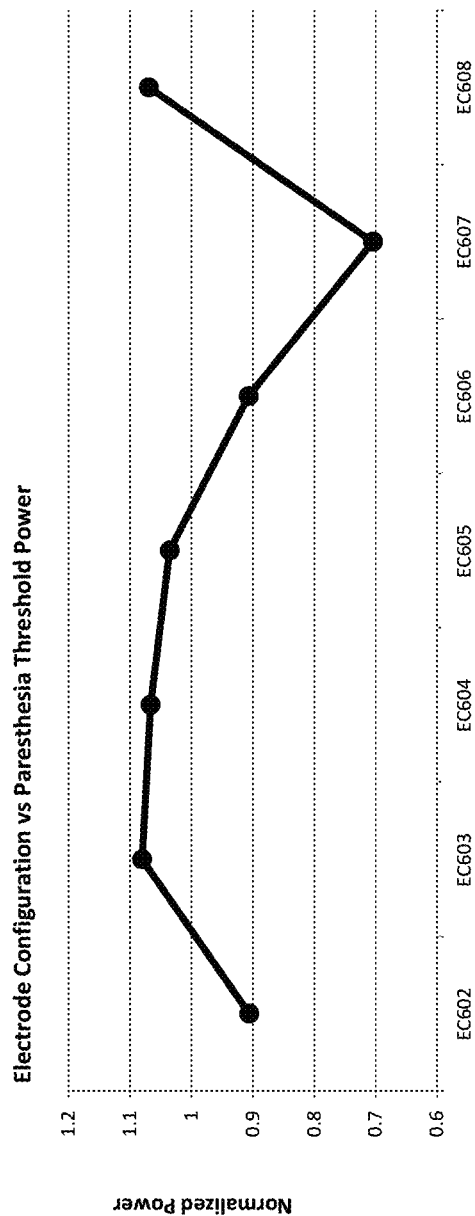

Particularly, as indicated in FIG. 7, the pulse generator 2 is configured to deliver said cathodic current pulses CP in a sequential fashion, i.e. as a sequential cathode train T, such that each electrode contact E1 . . . E4 of the two groups G1, G2 delivers a cathodic current pulse CP following a cathodic current pulse CP of the previous electrode contact and before an anodic charge balancing current pulse AP of the previous electrode contact.

Preferably, the respective electrode contact spacing CS as shown in FIGS. 5A to 5D (e.g. G1), which is defined as 2-20 mm, e.g. 2-3 mm, 7 mm, mm, is selected large enough to provide effective electric field penetration within and along the spinal cord for complete therapy coverage while minimizing spatial summation of neuron transmembrane potential changes between contacts, inter-pulse intervals are selected large enough to reduce neural refractory effects, and interleaved stimulation are set with symmetric charge balancing phases. The stimulation is sub-threshold, i.e. the stimulation amplitude is set under the perception threshold and therefore does not produce sensations that the patient can feel.

Furthermore, an embodiment of the method according to the present invention is illustrated in FIG. 7. According thereto, the stimulation (particularly SCS) begins with a cathodic phase CP, contains an Inter-pulse interval II, and ends with an anodic (charge balancing) phase AP, and repeats. The return electrode passes the same but opposite currents. The stimulation of the respective group G1 or G2 takes place in between the charge balancing phase of the preceding group G2 or G1.

In detail, the method comprises at least the steps of
delivering a current pulse CP of amplitude −A between at least two electrodes E1, E3 comprised by the first group G1,
delivering a current pulse CP of amplitude −B between at least two electrodes E2, E4 comprised by the second group G2, prior to charge balance AP of the first group G1

Furthermore, particularly, the following steps are performed:
delivering a charge balancing current pulse AP of amplitude A is next delivered to the first group G1, delivering a charge balancing current AP of amplitude B is next delivered to the second group G2, the current pulses are repeated in a cyclical manner.

As described before, the electrical stimulation preferably results in a sequential cathode train T shown in FIG. 7, wherein adjacent electrode contacts E1, E2, E3, E4 deliver cathodic stimulation CP following cathodic stimulation of a previous adjacent cathode and before the previous cathode delivers its anodic charge-balancing phase AP.

Stimulation parameters tested in the clinical study BEN-EFIT-01 aforementioned were assessed in a modeling study beforehand. This modeling study compared the activation thresholds of dorsal column (DC) axons of six of the tested electrode configurations (see FIG. 5(A): EC602, EC603, EC605, EC606, EC607, EC608. DC fibers activation is widely accepted in literature as the main mechanism for low-frequency (LF) SCS-induced pain relief [1], [2]. Although the mechanisms involved in high-frequency (HF) SCS and in the stimulation pattern according to the present invention might differ from LF SCS, DC fibers response remains a comparative indicator of stimulation-induced neuronal influence.

Figure 9:
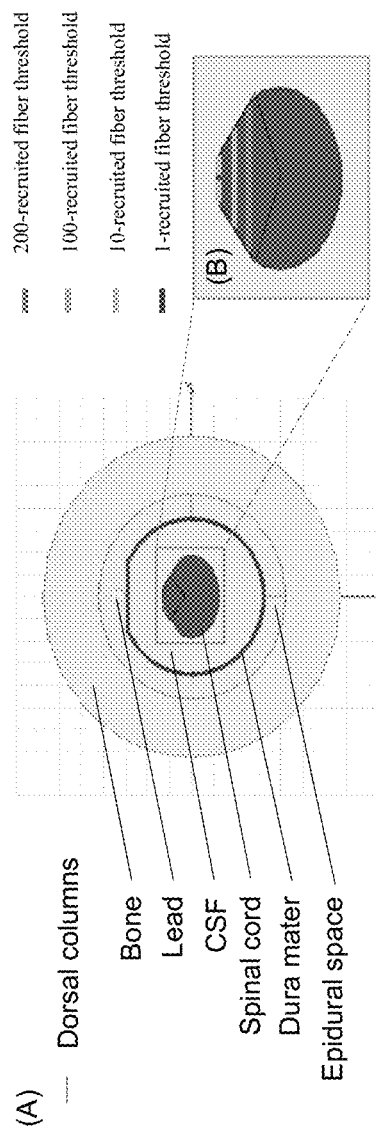
FIG. 9 shows the transverse section of the spinal cord model used for SCS simulations (A), and contours of recruitment areas of the most superficial 1, 10, 100 and 200 DC fibers (B)
Figure 10A:
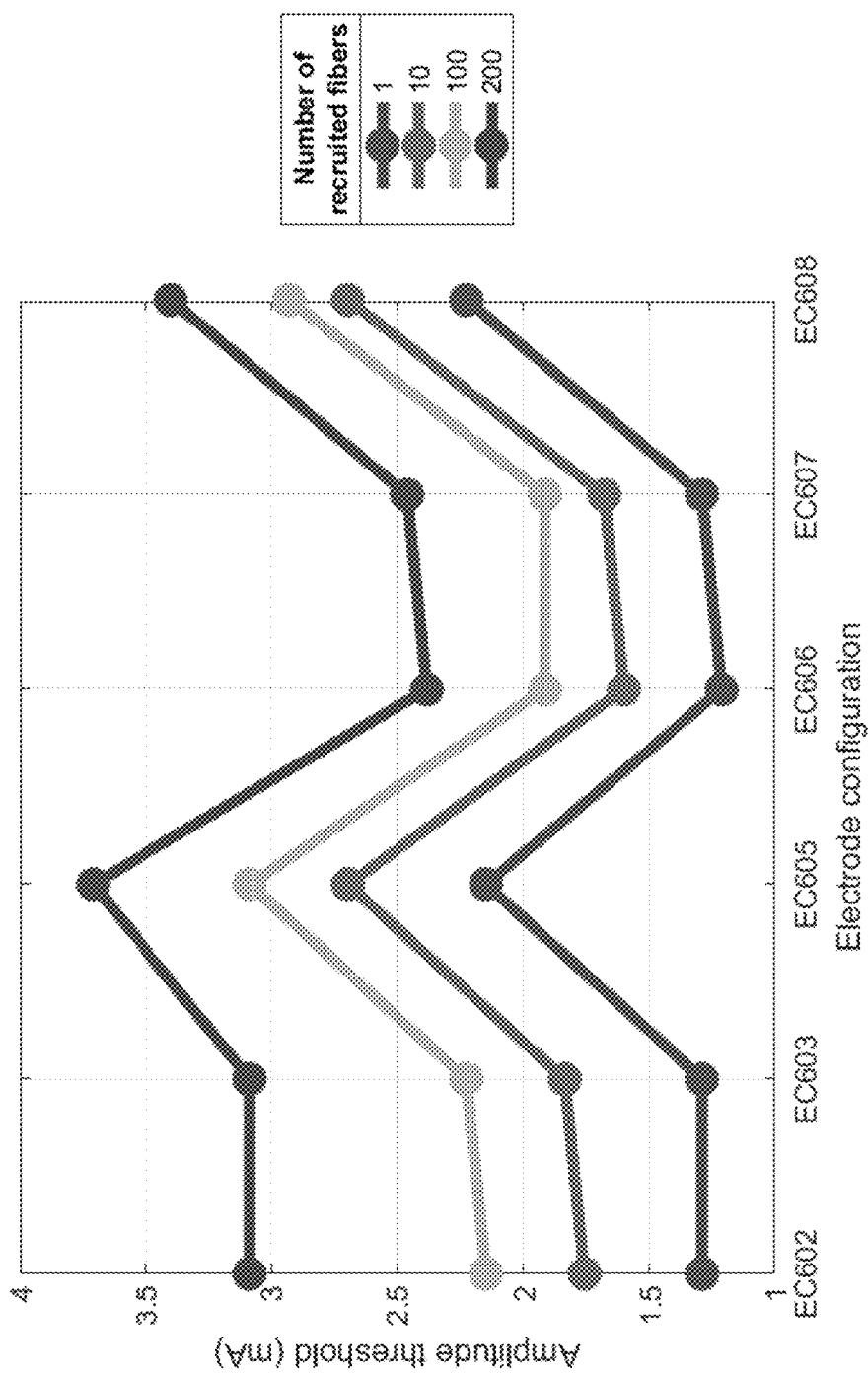
FIGS. 10A and 10B show stimulation amplitude (FIG. 10A) and electrical power (FIG. 10B), respectively, required to activate the most superficial (most dorsally located) 1, 10, 100 and 200-µm deep DC fibers, with different electrode configurations.
Figure 10B:
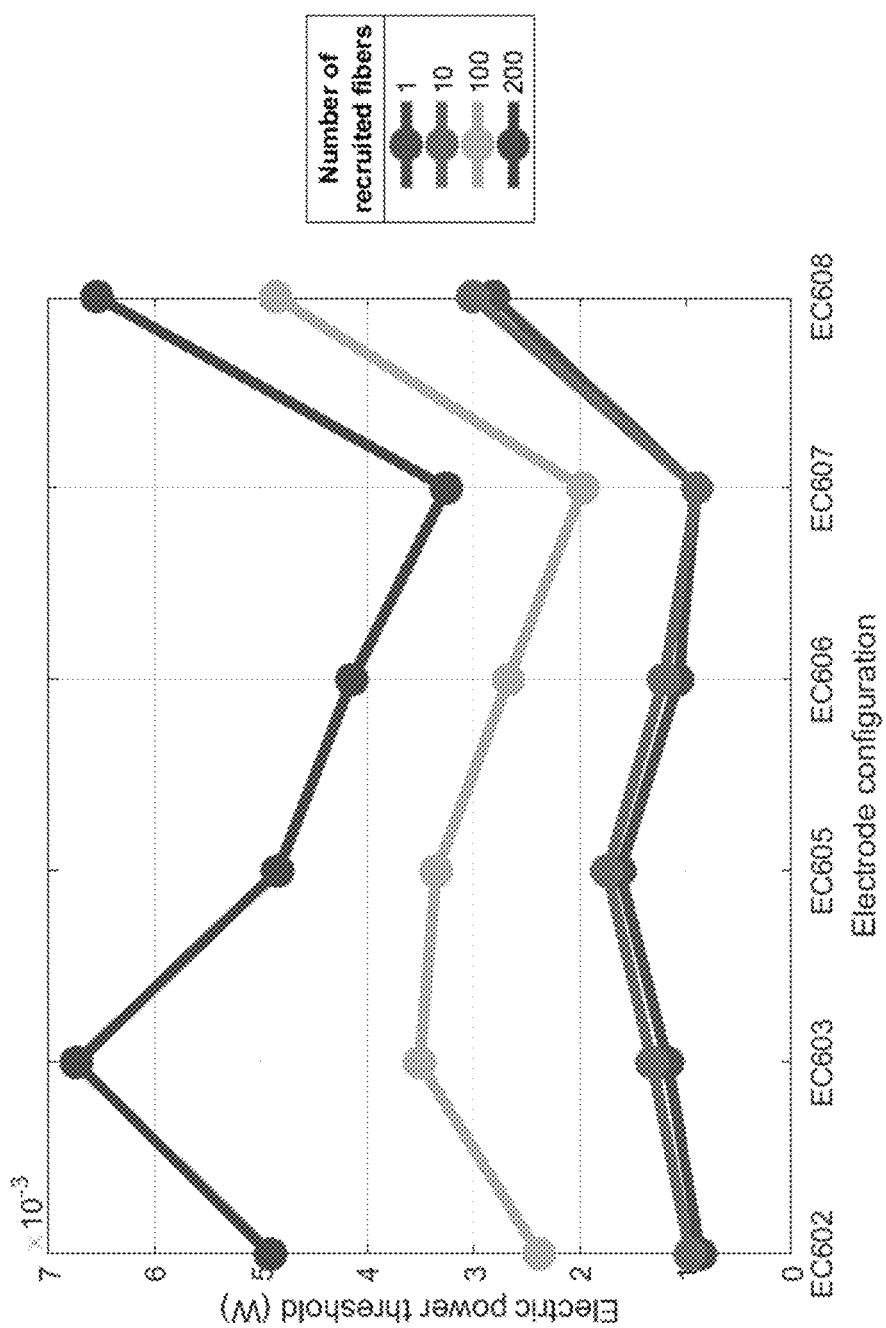

The simulations were all run using a mathematical axon model coupled to a 3D model of the spinal cord with one single implanted lead positioned against the dura mater on the spinal cord dorso-ventral midline (see FIG. 9). The activation threshold was calculated for a grid of neurons that covers the dorsal columns area, namely the dorsal column fibers. The amplitude and electrical power required to activate the first 1, 10, 100 and 200 neurons in the superficial dorsal column area (i.e. the fibers closest to the electrodes) are plotted in FIGS. 10A and 10B, respectively.

The results support the clinical findings that adjacent bipolar pair electrodes and multiple cathodes (EC603, EC605, EC608) are relatively inefficient configurations, compared to spaced one-cathode arrangements. These findings extend from the recruitment of one single fiber to the 200 most superficial DC neurons, which indicates that these relative performances persists whether the stimulation target is located on the superficial area of the spinal cord or deeper inside. The application of spaced bipolar electrode configurations in embodiments of the present invention will therefore help reduce SCS energy demand while maintaining equivalent or improved performance.

According to the invention, "spaced" electrode configuration is to be understood as at least two spatially separated electrodes. The distance between the electrodes can be e.g. 2-3 mm, 7 mm, 14 mm (measured center to center of the electrodes).

The present invention can be used to provide a novel SCS therapeutic stimulation approach which delivers pain relieving neuromodulation at high frequencies and with lower energy requirements and broader coverage compared to the current state-of-the-art.

This stimulation pattern according to the present invention provides a broader coverage of spinal cord segment levels (along the spinal cord axis) with cathodic stimulation, which is known to drive neuron depolarization. Because of the topographical distribution of fibers in the spinal cord, stimulating a larger longitudinal portion of the spinal cord implies that the activity of neural elements directly or indirectly connected to more dermatomes will be modulated by the stimulation. Moreover, because of the delayed onset time associated with sub-perception SCS and the possible discrepancy in neural target between sub-perception and paresthesia-based SCS therapies, the lead placement is usually not mapped with respect to low-frequency SCS-induced paresthesia, but is rather arbitrary placed at the T9-T10 vertebral junction. By covering a wider portion of the spinal cord levels, this new SCS therapy will be less sensitive to the variations in the analgesic sweet spot.

Particularly, due to the longer period between each pulse of one given electrode contact, the range of possible pulse widths W is larger than in high-frequency stimulation modes. With this new stimulation pattern, programming different pulse widths W will allow for a therapy that is more adaptable to the inter- and intra-patient variability and will therefore increase the rate of SCS responders in the short term, but also the long-term by adapting the stimulation settings to newly developed pain areas.

Figure 11:
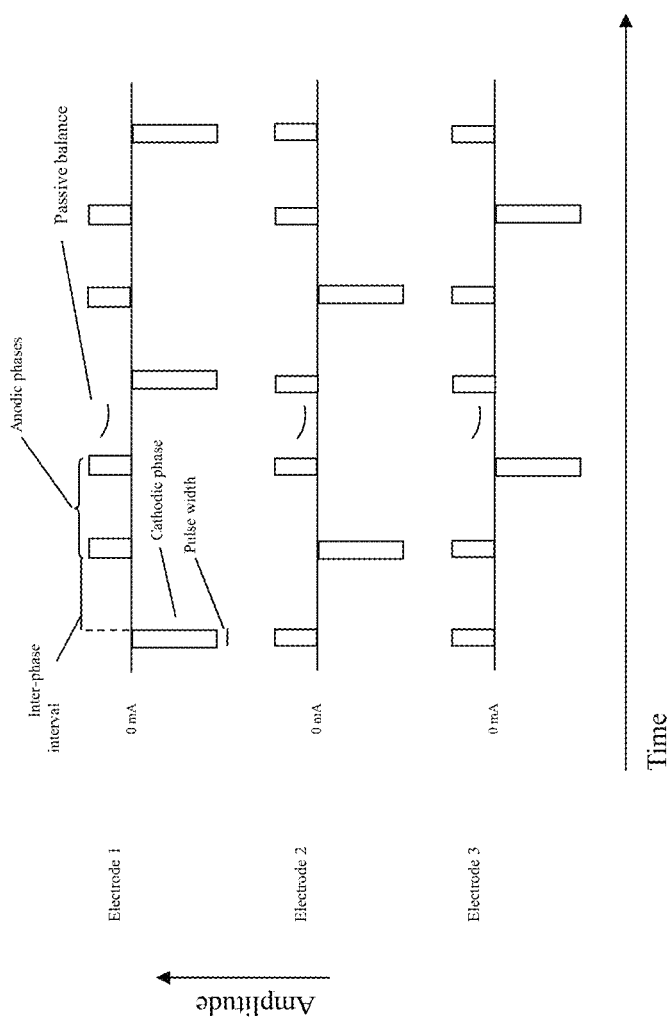
FIG. 11 is a diagram showing one embodiment of the novel stimulation waveform between three (3) electrodes, with cathodic preference.

FIG. 11 shows a diagram of one embodiment of the stimulation waveform according to the present invention between three (N=3) therapy electrodes, with cathodic preference. The exemplary system/device comprises three (3) electrodes (electrode 1, electrode 2, and electrode 3), each of the three (3) electrodes undergoes a recurring pattern of a cathodic phase (therapeutic phase, also denoted therapeutic electric pulse herein) with a current amplitude I and a series of two (2) charge balancing anodic phases (charge balancing phases, also denoted as charge balancing electric pulses herein), which pass ½ of the inverted current amplitude I of the therapeutic phase. The therapeutic phase and the charge balancing phases are separated by one (1) inter-phase interval. While electrode 1 passes the therapeutic phase with amplitude I, each of electrode 2 and electrode 3 passes one (1) charge balancing phase with amplitude I/2. While electrode 2 passes the therapeutic phase with amplitude I, each of electrode 1 and electrode 3 passes one (1) charge balancing phase with amplitude I/2. While electrode 3 passes the therapeutic phase with amplitude I, each of electrode 2 and electrode 1 passes one (1) charge balancing phase with amplitude I/2. After electrode 3 passed one (1) therapeutic phase the cycle starts with electrode 1 again, until terminated. In this way, charge neutrality on any given electrode is maintained, and the sum of current exiting the cathode equals the sum of currents entering anodes at any given time in the waveform.

Figure 12:
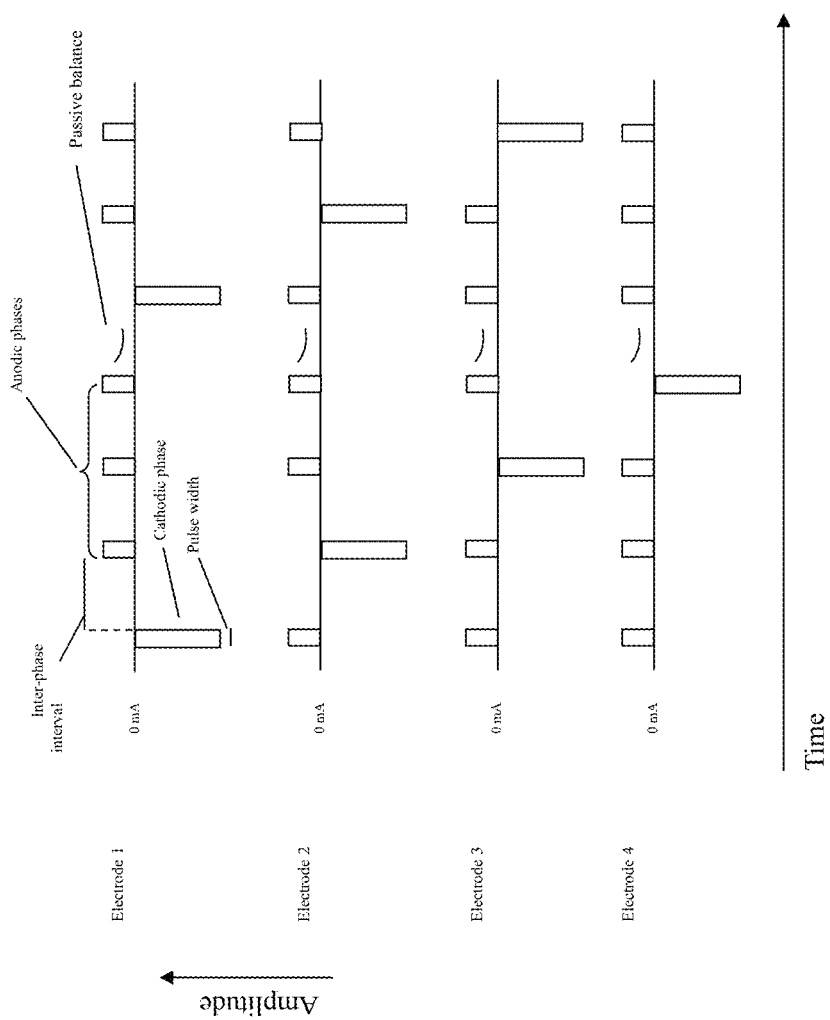
FIG. 12 is a diagram showing another embodiment of the novel stimulation waveform between four (4) electrodes, with cathodic preference.

FIG. 12 shows a diagram of another embodiment of the stimulation waveform according to the present invention between four (N=4) therapy electrodes, with cathodic preference. The exemplary system comprises four (4) electrodes (electrode 1, electrode 2, electrode 3, and electrode 4), each of the four (4) electrodes undergoes a recurring pattern of a cathodic phase (therapeutic phase, also denoted as therapeutic electric pulse herein) with a current amplitude I and a series of three (3) charge balancing anodic phases (charge balancing phases, also denoted as charge balancing electric pulses herein), which pass ⅓ of the inverted current amplitude I of the therapeutic phase. The therapeutic phase and the charge balancing phases are separated by one (1) inter-phase interval. While electrode 1 passes the therapeutic phase with amplitude I, each of electrode 2, electrode 3 and electrode 4 passes one (1) charge balancing phase with amplitude I/3. While electrode 2 passes the therapeutic phase with amplitude I, each of electrode 1, electrode 3 and electrode 4 passes one (1) charge balancing phase with amplitude I/3. While electrode 3 passes the therapeutic phase with amplitude I, each of electrode 1, electrode 2 and electrode 4 pass one (1) charge balancing phase with amplitude I/3. While electrode 4 passes the therapeutic phase with amplitude I, each of electrode 1, electrode 2 and electrode 3 pass one (1) charge balancing phase with amplitude I/3. After electrode 4 passed one (1) therapeutic phase the cycle starts with electrode 1 again, until terminated. In this way, charge neutrality on any given electrode is maintained, and the sum of current exiting the cathode equals the sum of currents entering anodes at any given time in the waveform.

Figure 13:
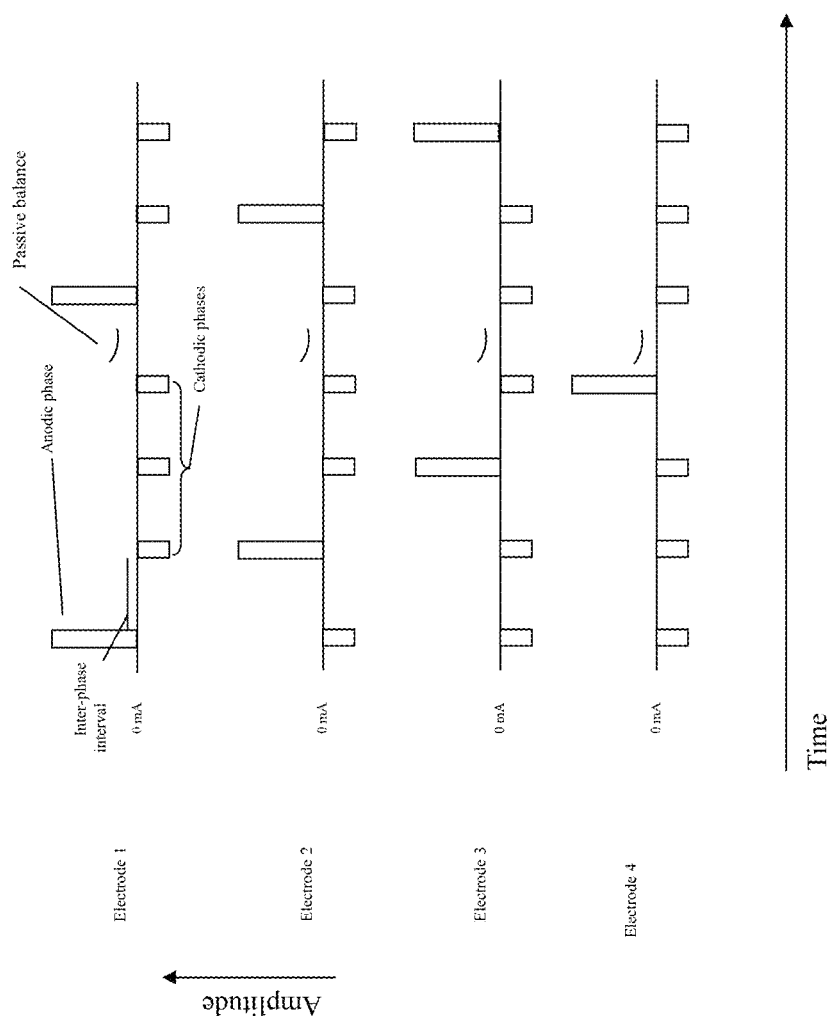
FIG. 13 is a diagram showing another embodiment of the novel stimulation waveform between four (4) electrodes, with anodic preference.

FIG. 13 shows a diagram of another embodiment of the stimulation waveform according to the present invention between four (N=4) therapy electrodes, with anodic preference. The exemplary system/device comprises four (4) electrodes (electrode 1, electrode 2, electrode 3, and electrode 4), each of the three (3) electrodes undergoes a recurring pattern of an anodic phase (therapeutic phase, also denoted as therapeutic electric pulse herein) with a current amplitude I and a series of two (2) charge balancing cathodic phases (charge balancing phases, also denoted as charge balancing electric pulses herein), which pass ⅓ of the inverted current amplitude I of the therapeutic phase. The therapeutic phase and the charge balancing phases are separated by one (1) inter-phase interval. While electrode 1 passes the therapeutic phase with amplitude I, each of electrode 2, electrode 3 and electrode 4 passes one (1) charge balancing phase with amplitude I/3. While electrode 2 passes the therapeutic phase with amplitude I, each of electrode 1, electrode 3 and electrode 4 passes one (1) charge balancing phase with amplitude I/3. While electrode 3 passes the therapeutic phase with amplitude I, each of electrode 1, electrode 2 and electrode 4 pass one (1) charge balancing phase with amplitude I/3. While electrode 4 passes the therapeutic phase with amplitude I, each of electrode 1, electrode 2 and electrode 3 pass one (1) charge balancing phase with amplitude I/3. After electrode 4 passed one (1) therapeutic phase the cycle starts with electrode 1 again, until terminated. In this way, charge neutrality on any given electrode is maintained, and the sum of current entering the anode equals the sum of currents exiting the cathodes at any given time in the waveform.

Alternatively, anodic and cathodic preferences can be mixed or combined in different sequences and alternatively, the amplitudes of the charge balancing phases can have different values for each phase.

Figure 14:
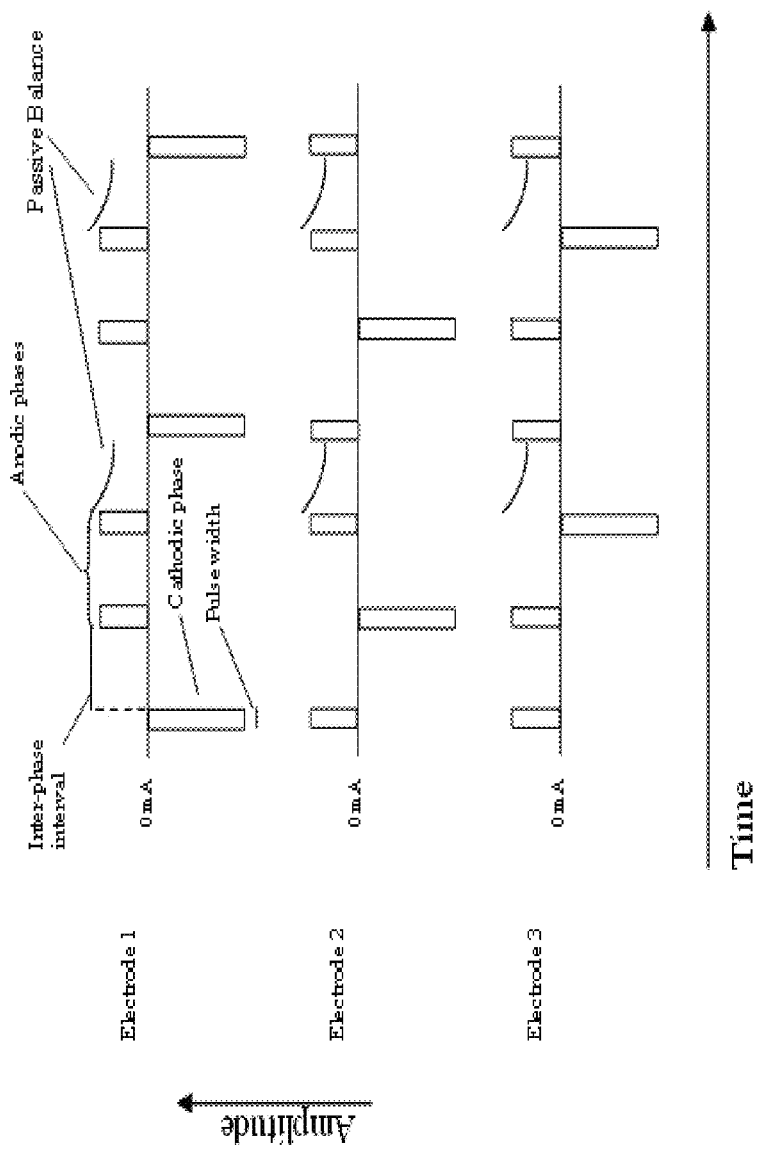
FIG. 14 is a diagram showing another embodiment of the novel stimulation waveform between three (3) electrodes, with cathodic preference.

FIG. 14 shows a diagram of another embodiment of the novel stimulation waveform between three (3) electrodes, with cathodic preference. Stimulation begins with a cathodic phase, contains an inter-phase interval, and ends with a series of anodic (charge balancing) phases, which are aligned with the cathodic phase of a different electrode. In this example, each return electrode (electrode 2 and electrode 3 when electrode 1 stimulates) passes ½ of the amplitude and opposite currents as the currently active cathodic electrode, and the second anodic phase is delivered with passive balancing which may last longer than the cathodic phase of the opposing electrode. In this way, charge neutrality on any given electrode is maintained, and the sum of current exiting the cathode equals the sum of currents entering anodes at any given time in the waveform.

Figure 15:
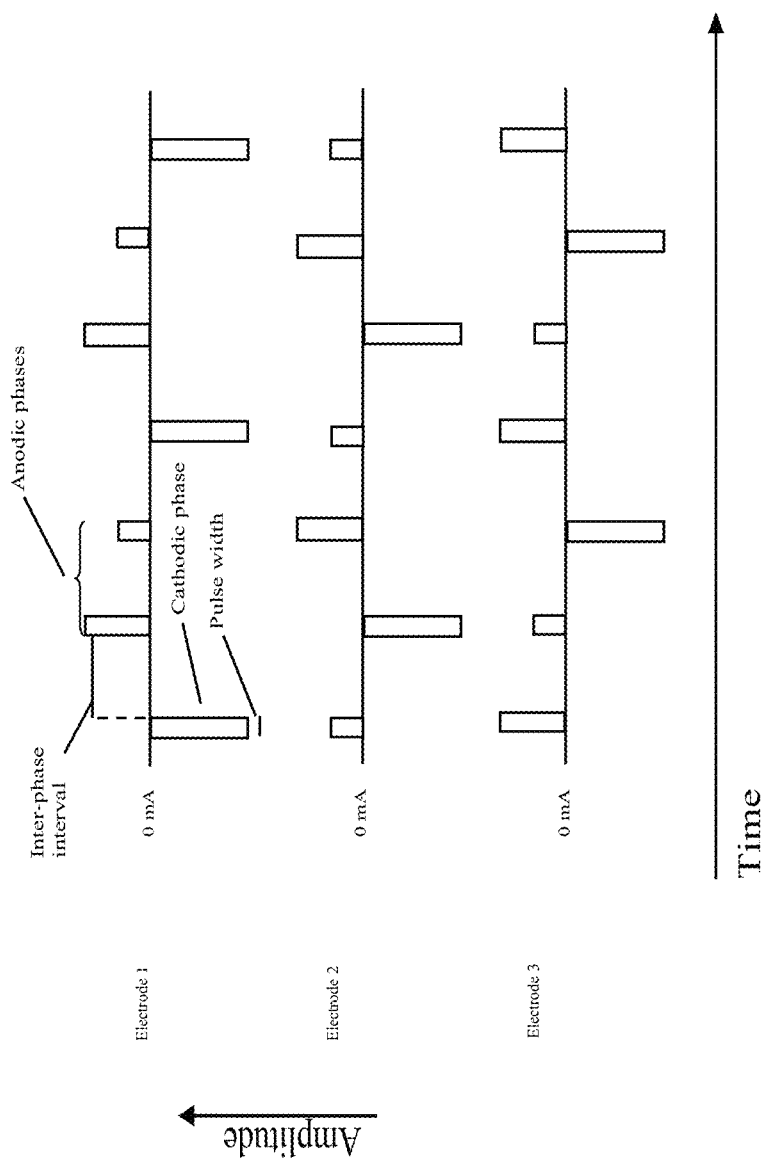
FIG. 15 is a diagram showing another embodiment of the novel stimulation waveform between three (3) electrodes, with cathodic preference.

FIG. 15 shows a diagram of another embodiment of the novel stimulation waveform between three (3) electrodes, with cathodic preference. Stimulation begins with a cathodic phase, contains an inter-phase interval, and ends with a series of anodic (charge balancing) phases, which are aligned with the cathodic phase of a different electrode. In this example, return currents do not share equal current yet the sum of their current equals the amplitude and is opposite the current of the currently active cathodic electrode. In this way, charge neutrality on any given electrode is maintained, and the sum of current exiting the cathode equals the sum of currents entering anodes at any given time in the waveform.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A medical device for generating electrical stimulation of a patient, the medical device comprising:
    a pulse generator configured to generate current pulses for electrical stimulation of the patient; and
    at least one electrode lead configured to be connected to the pulse generator and having a plurality of electrode contacts for delivering the current pulses to tissue of the patient;
    said electrode contacts including at least two interleaved groups, with one contact of a first said group being disposed between two contacts of a second said group;
    said pulse generator being configured to generate said current pulses with a rate in the range from 1 Hz to 100 kHz, and individual current pulses having a pulse width in a range from 10 µs to 10 ms; and
    said pulse generator being configured to generate a stimulation pulse between said electrode contacts of said first group, followed by a stimulation pulse between said electrode contacts of said second group, and to subsequently generate a charge balance pulse between the electrode contacts of said first group, followed by a charge balancing pulse between said electrode contacts of said second group, wherein the stimulation pulse and the charge balancing pulse have opposite polarity.

2. The medical device according to claim 1, wherein the rate lies in a range from 50 Hz to 1470 Hz, and wherein the pulse width lies in a range from 30 µs to 1000 µs.

3. The medical device according to claim 1, wherein a respective current pulse has an amplitude in a range from 0.01 mA to 20 mA.

4. The medical device according to claim 3, wherein the amplitude lies in a range from 0.1 mA to 10 mA.

5. The medical device according to claim 1, wherein said pulse generator is configured to deliver a current pulse between two electrode contacts of said plurality of electrode contacts and a subsequent current pulse between two further electrode contacts of said plurality of electrode contacts, before delivering a charge balancing current pulse between said two electrode contacts.

6. The medical device according to claim 1, wherein the rate is 1470 Hz and the pulse width is 90 µs.

7. The medical device according to claim 1, wherein the rate is 625 Hz and the pulse width is 200 µs.

8. The medical device according to claim 1, wherein said pulse generator is configured to successively deliver the current pulses via the different electrode contacts, wherein for each of the current pulses at least two charge balancing current pulses are delivered simultaneously with the stimulating current pulse delivered via one of the different electrode contacts.

9. The medical device according to claim 8, wherein the rate is 300 Hz and the pulse width is 300 µs.

10. The medical device according to claim 8, wherein the at least two charge balancing pulses are completed within 10 ms of an end of one of the current pulses.

11. The medical device according to claim 8, wherein the rate is 556 Hz and the pulse width is 300 µs.

12. The medical device according to claim 1, wherein said pulse generator is configured to deliver said current pulses to a central nervous system of the patient such that no paresthesia is induced in the patient.

13. The medical device according to claim 1, wherein said pulse generator is configured to deliver said current pulses to a central nervous system of the patient and to thereby induce paresthesia in the patient.

14. The medical device according to claim 1, wherein said at least one electrode lead is configured to be implanted along a spinal cord of the patient and to deliver the current pulses to a longitudinal region of the spinal cord which is greater than one vertebral body of the patient.

15. The medical device according to claim 1, wherein neighboring electrode contacts of said at least one electrode lead and/or simultaneously active electrode contacts are separated by a spacing distance in a range from 7 mm to 14 mm.

16. The medical device according to claim 1, wherein said pulse generator is configured to deliver current pulses during an on-period and to suspend a delivery of the current pulses during on off-period in an alternating fashion, wherein a time span during which the current pulses are delivered by the pulse generator during the respective on-period has a length that corresponds to 10% to 100% of a length of the respective on-period.

17. The medical device according to claim 16, wherein the length during which the current pulses are delivered is 25% to 100% of the length of the respective on-period.

18. The medical device according to claim 16, wherein the length during which the current pulses are delivered is 30% to 100% of the length of the respective on-period.

19. The medical device according to claim 16, wherein the length during which the current pulses are delivered is 10% to 60% of the length of the respective on-period.

20. A method for controlling electrical stimulation pulses, the method comprising:

providing a medical device according to claim 1;

successively delivering current pulses via different electrode contacts, wherein for each current pulse at least one charge balancing current pulse is subsequently delivered via the respective electrode contact; and delivering the current pulses at a rate in a range from 1 Hz to 100 kHz, and with individual current pulses having a pulse width in a range from 10 μs to 10 ms.

* * * * *